US012539184B2

(12) United States Patent
Pickert et al.

(10) Patent No.: US 12,539,184 B2
(45) Date of Patent: Feb. 3, 2026

(54) COMPUTER-IMPLEMENTED METHOD FOR THE REMOTE CONTROL OF AN INTERVENTION DEVICE, AND INTERVENTION SYSTEM

(71) Applicant: Siemens Healthcare GmbH, Erlangen (DE)

(72) Inventors: Nils Sebastian Pickert, Erlangen (DE); Gaurav Tripathi, Erlangen (DE); Andreas Berting, Schlüchtern (DE); Winfried Lurz, Fürth (DE); Markus Solowiej, Neunkirchen am Brand (DE); Michael Greiffenhagen, Hirschaid (DE)

(73) Assignee: Siemens Healthineers AG, Forchheim (DE)

( * ) Notice: Subject to any disclaimer, the term of this patent is extended or adjusted under 35 U.S.C. 154(b) by 202 days.

(21) Appl. No.: 18/221,641

(22) Filed: Jul. 13, 2023

(65) Prior Publication Data

US 2024/0016558 A1 Jan. 18, 2024

(30) Foreign Application Priority Data

Jul. 15, 2022 (DE) ..................... 10 2022 207 264.2

(51) Int. Cl.
*A61B 34/35* (2016.01)
*A61B 34/20* (2016.01)
*A61B 34/30* (2016.01)

(52) U.S. Cl.
CPC .............. *A61B 34/35* (2016.02); *A61B 34/20* (2016.02); *A61B 2034/2055* (2016.02); *A61B 2034/301* (2016.02)

(58) Field of Classification Search
CPC . A61B 34/35; A61B 34/20; A61B 2034/2055; A61B 2034/301;

(Continued)

(56) References Cited

U.S. PATENT DOCUMENTS

2023/0165649 A1* 6/2023 Fitzsimons ............ A61B 34/30 700/245

FOREIGN PATENT DOCUMENTS

CN 106597972 A * 4/2017 ........... G05B 19/048

OTHER PUBLICATIONS

CN 106597972 A—english trans (Year: 2017).*
Decision to Grant German Patent App. DE 10 2022 207 264.2 mailed Mar. 11, 2025, with English translation.

* cited by examiner

*Primary Examiner* — Abby Lin
*Assistant Examiner* — Renee LaRose
(74) *Attorney, Agent, or Firm* — Lempia Summerfield Katz LLC

(57) ABSTRACT

A computer-implemented method for generating control information for the remote control of an intervention device that is to be used during an intervention, for example a medical intervention, at an intervention location, wherein at least one first person is present at the intervention location and at least one second person is present at a location which differs from and is remote from the intervention location for the purpose of cooperation during the performance of the intervention, and control information provided by the second person is sent from the remote location to the intervention location by a communication connection, wherein use of the control information for controlling the intervention device is only enabled if a safeguarding signal, which indicates a monitoring activity of the first person and is output by a signaling device that may be activated by the first person, is present.

17 Claims, 3 Drawing Sheets

(58) Field of Classification Search
CPC ........... A61B 2017/00123; A61B 2017/00203; A61B 2017/00207; A61B 2017/00973; A61B 2090/376; G16H 40/67
See application file for complete search history.

COMPUTER-IMPLEMENTED METHOD FOR THE REMOTE CONTROL OF AN INTERVENTION DEVICE, AND INTERVENTION SYSTEM

CROSS REFERENCE TO RELATED APPLICATIONS

This application claims the benefit of DE 10 2022 207 264.2 filed on Jul. 15, 2022, which is hereby incorporated by reference in its entirety.

FIELD

Embodiments relate to a computer-implemented method for the remote control of an intervention device that is to be used during an intervention, for example a medical intervention, at an intervention location, with at least one first person present at the intervention location and with at least one second person present at a location which differs from and is remote from the intervention location for the purpose of cooperation during the performance of the intervention.

BACKGROUND

Many interventions, for example medical minimally invasive interventions, require great expertise which is not always available at the intervention location itself. It has therefore already been proposed to allow "distributed" performance of such interventions, specifically by additionally calling on the expertise of at least one second person at a remote location. It is customary e.g., during medical interventions, for example minimally invasive interventions, e.g., for the purpose of diagnosis and/or therapy, to insert medical instruments into the human body. Such instruments may include e.g., guide wires, catheters, needles, and the like. Examples of minimally invasive medical interventions include the placement of stents and the detection of stenoses. When working in the vascular system, e.g., navigation may be achieved by rotating and advancing a guide wire or the medical instrument, e.g. a catheter, at the actual point of insertion, e.g. the groin of the patient. It has already been proposed to support such interventions by a robot that may assume responsibility for example for the manipulation of the at least one inserted medical instrument. For the purpose of monitoring the procedure, possible intervention devices include e.g. imaging devices, for example x-ray devices including a C-arm. These supply highly accurate supplementary information, including situational data that largely covers the region of influence of the medical robot, for example the operating region of the medical instrument. In this respect, it has already been proposed to provide the situational data to the second person at the remote location and to relinquish control of the robot entirely to the second person with their greater expertise. Such robots have the advantage of performing actions derived from control information provided by the second person rather more slowly, and therefore any possible latency in the communication connection between the remote location and the intervention location is not an obstacle to remote control.

For example with regard to other intervention devices, e.g. imaging devices and treatment devices that involve radiation and/or mobile recording components or treatment components, such remote control systems must be considered susceptible to problems, since the available situational data that may be transferred to the second person by the communication device might not cover the entire region of influence and region of effect of the intervention device, or because functions are implemented on a timescale that is significantly faster than a latency that may be present on the communication connection. For example, safety-relevant functions of intervention devices usually require special safety measures, e.g., multi-channel systems and/or control with protection against individual errors. Even precise monitoring by the person who initiated the function is often necessary. Such functions of intervention devices include for example movement functions and radiation-based functions, for example x-ray functions. It may occur here that e.g., the movement of components, e.g., recording components and/or treatment components, is blocked by a person or an object, and/or that the radiation safety is not satisfied in the case of radiation-based functions because e.g., a person and/or an object, incompatible with the radiation safety, is situated at the intervention location, for example in the region of influence or region of effect of the intervention device.

If remote control by the second person at the remote location is allowed, such safety requirements may not necessarily be satisfied due to situational data that does not cover the whole region of influence or region of effect, latencies of the communication connection and/or reliability of the line at the remote location. If e.g., the second person at the remote location initiates a safety-relevant function, the effectiveness of the monitoring by the second person may be significantly limited, e.g., by a restricted field of a camera supplying situational data and/or other technical restrictions, in comparison with local initiation of the safety-relevant function by the first person.

It is therefore proposed in the prior art, with regard to such intervention devices that are fast-acting and/or whose region of influence and/or region of effect cannot be fully captured in situational data at the remote location, to allow only parameterizations by the second person while the initiation of the function is then performed by the first person at the intervention location. This may result in problems as described below using the example of a planned movement of a recording component and/or treatment component of an intervention device.

In this case, the second person at the remote location initially establishes that a movement is necessary. The first person at the intervention location is thereupon requested verbally via the communication connection to undertake the necessary movements. The first person then executes the movement at the intervention device by local control as per instructions. The remote second person observes the movement with reference to the situational data, to the extent that this is possible. A renewed assessment of the necessity for a movement must then be undertaken if applicable, resulting in further corrective instructions and local control measures. This solution therefore demands onerous coordination between the intervention location and the remote location and makes the activity more complicated, particularly for the second person. Particular complexity arises if a medical instrument has to be guided by a medical robot via remote control, since an image recording made by an imaging device as an intervention device then requires recording components to be accurately positioned in advance, for example for the purpose of tracking, before the radiation may be initiated for the purpose of image recording.

In summary, the workflow becomes highly complex as a result of the coordination that is required, and an expert must also be present at the intervention location to execute the functions of the intervention devices.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a possibility, that satisfies safety requirements, for the remote control of an intervention device, for example if the region of influence and/or region of effect of the intervention device cannot be fully captured by situational data at the remote location.

A method is provided for generation of the control information for controlling the intervention device to be enabled only if a safeguarding signal, that indicates a monitoring activity of the first person and is to be output by a signaling device that may be activated by the first person, is present.

The control information may relate for example to functions of the intervention device that are initiated by the control information and for example have safety requirements in respect of their execution. Such functions may be e.g., those that include the initiation of radiation, for example x-radiation, and/or relate to a movement of at least one component of the intervention device. For example, the method provides for situational data to be recorded by at least one situational data capturing apparatus and transferred to the remote location where it is displayed to the second person, wherein the situational data does not cover the entire region of influence and/or region of effect of the intervention device. Additionally, or alternatively, a communication connection may be used whose latency is e.g. more than 300 ms, for example at least 500 ms. The communication connection may be for example a normal telephone and/or internet connection. The communication connection is therefore for example a single-channel connection.

In order that requirements relating to functional safety, particularly in respect of monitoring and the possibility of swift action, may also be satisfied under such adverse circumstances as per the examples, the first person may be employed as a monitoring person and to check and if possible provide their presence and monitoring activity by technical measures. In other words, the first person is the "eyes and ears" of the second person. It is thus possible to provide greater reliability of operation for the intervention device, achieving safety even in the event of an individual error, e.g., on the part of the second person, since in this example the first person monitors the implementation of the control information.

In order to provide as far as possible the presence and monitoring activity of the first person, a signaling device is provided that may be activated by the first person so that it is possible to provide a corresponding safeguarding signal that is logically combined with the control information (remote control signal), e.g. as an "AND" operation forming a prerequisite for the implementation of the control information. In this way, a possibility is provided for combined monitoring of the functionality of the intervention device by the second person and by the first person, the first person is able for example to cover parts of the region of influence and/or region of effect of the intervention device that are not captured in the situational data and/or to react quickly.

Embodiments allow the generation of control information for the direct remote control of the intervention device by the second person, for example for the purpose of executing functions that include safety-relevant functions, because the local first person provides additional monitoring in order for example to cover regions that are not covered for the remote location by the feedback channels, i.e., the situational data. For example, the first person may check that no unprotected person and/or no unprotected object is present in the region of influence and/or region of effect when radiation is initiated. In general terms, the first person has the possibility to prevent or to stop the execution of the implementation of the control information in case of danger or risk.

The signaling device and a control device may evaluate the safeguarding signal appropriately and provide that the first person is present and attentive. For example, less expertise is required at the intervention location, since complex control operations may be initiated by the second person and then need only be monitored by the first person. In the case of e.g., medical interventions, the at least one first person often has such expertise anyway.

Embodiments relate to control information for the performance of a medical intervention, for example on a patient. For example, the medical intervention may be a minimally invasive examination or a minimally invasive procedure in this case. For example, the medical intervention may relate to a treatment and/or diagnosis. The medical intervention may be the insertion of an implant, e.g., a stent, and/or an examination involving a medical instrument, for example a catheter. The intervention may include a multiplicity of work stages, possibly building up on each other and for example interdependent.

The remote location is situated remotely from the intervention location, this meaning for example that there is no direct visual and/or acoustic contact between the first person and the second person. The second person and therefore the remote location may be situated in a different room and/or a different building and/or a different town and/or a different country and/or on a different continent than the first person, i.e., the intervention location. The communication connection may also allow the first and second persons to communicate with each other visually and/or acoustically.

In an embodiment, the intervention device may be an imaging device including a radiation-based and/or mobile recording component. In the case of radiation-based imaging devices, e.g., x-ray devices, that region of influence and/or region of effect of the imaging device that is affected by the radiation is often not fully captured by the situational data. In addition, such imaging devices offer a multiplicity of degrees of freedom for the movement of recording components, e.g., by providing a C-arm on which an x-ray source and an x-ray detector are arranged opposite each other as part of an x-ray device. Furthermore, in the case of complex high-precision three-dimensional positioning, correct interpretation of for example two-dimensional and/or relative situational data is at least made more difficult. Application to such intervention devices is therefore particularly advantageous.

With regard to the imaging device as an intervention device, the imaging device is provided in addition to an intervention robot that is likewise remotely controllable. For example, the intervention device may form part of a mobile treatment device, e.g. a mobile catheter laboratory, in which an intervention robot is used to control (for example navigate and apply) at least one medical instrument during a minimally invasive intervention, and corresponding monitoring image material is output by the imaging device, e.g. an x-ray device including a C-arm, which image material may e.g. at least partly provide the basis for remote control of the intervention robot. For example, such mobile intervention systems may be used to treat strokes and the like. In this context, embodiments make it possible while providing adequate functional safety to transfer the remote control not only for the intervention robot to the second person, but also the remote control of the imaging device, thereby allowing the procedure to be performed in a much simpler and intuitive manner.

For the purpose of generating the safeguarding signal by the signaling device, various advantageous developments are conceivable.

According to an embodiment, an operating element that must be lastingly activated, for example a foot switch, is used as an operating element of the signaling device that must be activated by the first person. In this development, the first person lastingly provides a confirmation of their presence for as long as they are actively monitoring, such that the control information is only implemented if it is present as a remote control signal and the safeguarding signal is present as a local confirmation signal. For example, a local (i.e. situated at the intervention location) foot switch of the intervention device, e.g. an x-ray device, may be activated as an operating element of the signaling device in this case, it is possible in embodiments for example to provide an operating device, via which the control information may be output, at the remote location also. This remote operating device may likewise include a foot switch, for example. When initiating x-radiation, e.g. the safeguarding signal of the local foot switch and the control information of the remote foot switch may then be logically combined ("AND") as a control signal in order to initiate the x-radiation.

In order to further improve the functional safety, for the purpose of checking the presence of the first person, prompting the first person by an indicator output, and for example periodically to briefly interrupt the activation of the operating element, the presence of the interruption is checked and the safeguarding signal deactivated if the interruption is not detected within a time window that follows the indicator. For example, the indicator output may take place periodically at predefined time intervals, e.g., 10 to 60 seconds.

With regard to the functional safety, further measures may be used to avoid an erroneous continuous state in which the safeguarding signal is lastingly present although the first person is not actively monitoring. In order to prevent the first person from keeping the operating element continuously activated, the requirement for a regular interruption in the activation of the operating element may be implemented. This is equivalent to a known automatic vigilance device in the context of driving a rail vehicle, it is necessary to release a continuously depressed driving pedal for a short time when a specified time interval has expired or after a specified distance has been covered. In an appropriate embodiment, an indicator output is used for this purpose, so that the monitoring first person may devote themselves entirely to their monitoring activity without simultaneously having to concentrate on the expiry of time intervals. For example, the time window following the output of the indicator to the first person via a suitable output may have a duration of a number of seconds, e.g. 1 to 4 seconds. If no interruption in the activation of the operating element is detected within this time, the safeguarding signal is deactivated.

In this first development, the operating element of the signaling device may simultaneously also be used advantageously to at least partly prevent the implementation of the control information and/or even at least partly to deactivate the intervention device, e.g., in the manner of an emergency-off switch. For example, in the event of a cessation in the activation of the operating element, for example for longer than a predetermined time duration, the drivability of the intervention device is suspended and/or the intervention device is at least partly deactivated. Specifically with regard to imaging devices as intervention devices, e.g. concerning the foot switch of the x-ray device cited above, it is customary to make the possibility of radiation output dependent on the lasting activation of a corresponding foot pedal as an operating element, and therefore this operating element may be assigned more generally to a dual use in this context.

The operating element of the signaling device also corresponds to an emergency-stop or emergency-off function, since it is no longer possible for example to implement or start safety-critical functions, for example relating to radiation and/or movement, when the operating element is released. If the monitoring person therefore establishes that e.g., a danger or risk could arise, e.g. because an additional person is situated in an exposed position at the intervention location when initiating radiation, the monitoring person merely has to release the operating element or cease the activation, in order to avoid the implementation of the control information or to immediately terminate the implementation process that is already in progress.

If checking the presence of the first person by an indicator output prompts the brief interruption in the activation of the operating element, any indicator output may be prevented while control information provided by the second person is implemented. It is thereby possible to avoid accidentally initiating a rejection/interruption due to the brief cessation in activation of the operating element, without this being intended.

In an embodiment, the signaling device may include an operating element configured as a dead man's switch, for example an operating button, the safeguarding signal is generated when activation of the operating element is detected, for example periodically and/or following an indicator output. Specifically, the safeguarding signal may be generated for a predetermined time period following activation of the operating element, for example 10 to 60 seconds, an indicator output taking place after this time period expires unless a further activation of the operating element has been detected, and the safeguarding signal is ceased when a time window following the indicator output has elapsed. The length of the time window may again be a number of seconds, e.g. 1 to 4 seconds.

In this implementation, the first person does not therefore confirm their monitoring activity continuously, but only for specific short intervals, thereby resulting in a time period during which the remote control is permitted due to the presence of the safeguarding signal. For example, the first person has to activate the operating element every n seconds in order to confirm that the first person is present and monitoring the intervention device, for example in a position to prevent or interrupt the implementation of control information, e.g. by activating a corresponding emergency operating element (emergency-off switch).

In this context, it is particularly advantageous if an operating element that is situated in the vicinity, for example the immediate vicinity, of an emergency-off switch of the intervention device is used as the operating element of the signaling device, for example such that the emergency-off switch is situated within reach of the first person when they are activating the operating element. For example, the operating element of the signaling device may be situated within a radius of less than a meter, for example less than 50 centimeters, from the emergency-off switch. It is thus provided that the first person is situated in a position from which the emergency-off switch may also be activated quickly if a problem arises or threatens to arise.

If the time period has expired, the first person must activate the operating element again, it is possible for an acoustic and/or optical indicator output to remind the first person that the confirmation is running out. A short time window may be allowed for the purpose of activating the operating element again. This development is therefore comparable with a dead man's switch, as used in rail vehicles.

In a third embodiment, if the first person receives specific knowledge of the content of the control information, a confirmation may also be effected by the signaling device on a "per case" basis. This is appropriate for example if the intervention device may be voice controlled, i.e. is able for example to interpret spoken words of an operator and convert them into corresponding control measures. In this context, the control information may be sent as a voice command that is evaluated by the intervention device, the voice command is output in a manner that is also audible to the first person at the intervention location, and the safeguarding signal is generated in a manner that is specific to the voice command when an operating element of the signaling device is activated. For example, the second person may therefore speak a voice command that is transferred via the communication connection and is acoustically output at the intervention location, such that it may be both received and interpreted by the intervention device and heard by the first person. The monitoring first person does not give a confirmation if problems are foreseen, but if the situation is considered to be free of problems, the monitoring first person may generate the safeguarding signal in a manner specific to the voice command by activating the operating element, e.g. an operating button, of the signaling device, and thereby approve this voice command as control information that is to be implemented.

In this context, it may also be appropriate for the operating device that is arranged at the remote location, and via which control information (for example for the intervention robot) may also be provided in a different way, to have a voice command confirmation element, e.g. a button or switch, in order to additionally confirm that a voice command was actually given. This confirmation may form part of the control information or simply identify the voice command as control information.

The image data of the first person may be evaluated by the signaling device, in order to detect gestures of the first person that identify the signal generation of the safeguarding signal. This means that operating elements for the signaling device may also be realized jointly with gesture recognition using corresponding imaging sensors, for example a 3D camera. For example, in the first embodiment, continuous activation of the operating element may mean continuously maintaining specific gestures, e.g. a raised right hand or left hand. Lowering of the hand then signifies a cessation of the activation. With regard to the second or third embodiments, e.g. a specific gesture may likewise be used to cause the activation of an operating element, e.g. making an OK sign with the fingers and/or giving a "thumbs up".

In addition to the method, embodiments provide an intervention system including an intervention device at an intervention location, the intervention device is used for an intervention, for example a medical intervention, and is operable by a first person at the intervention location, an operating device at a location that differs from the intervention location and is remote therefrom, the operating device is usable by a second person to provide control information for the intervention device, a communication connection for sending the control information from the remote location to the intervention location, and a control device that is configured to use the control information for the purpose of controlling the intervention device. The intervention system is characterized in that the intervention system also includes a signaling device that may be activated by the first person, the control device is configured to use the control information for the purpose of controlling the intervention device only if a safeguarding signal, that indicates a monitoring activity of the first person and may be generated by activating the signaling device, is present. All of the explanations relating to the method may be applied similarly to the intervention system, such that this likewise allows the previously cited advantages to be achieved. For example, the control device is therefore configured to perform the method and may be configured accordingly also to perform the preferred developments described above.

DETAILED DESCRIPTION

Figure 1:
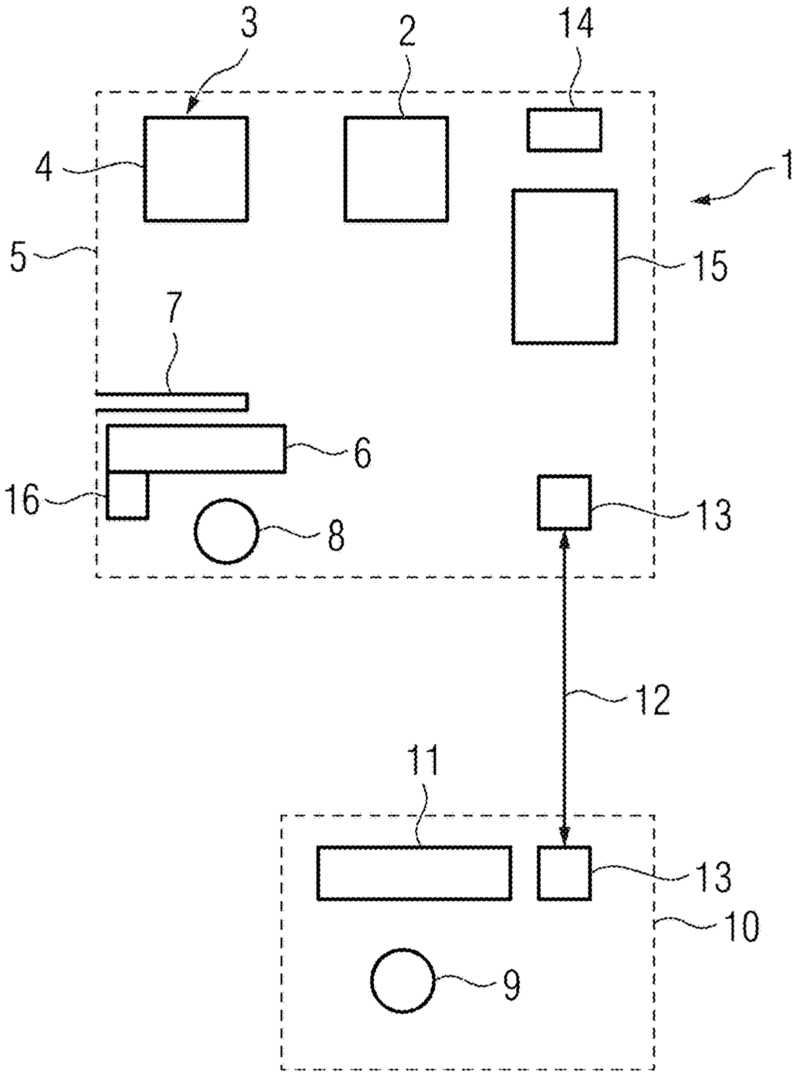
FIG. 1 depicts a schematic diagram of an intervention system according to an embodiment.

FIG. 1 depicts an intervention system 1 for performing an intervention, here a medical intervention on a patient. The intervention system 1 is specifically configured to perform a minimally invasive procedure as a medical intervention. At least one medical instrument, e.g. a catheter, may be moved and operated within the patient by an intervention robot 2. For the purpose of tracking the at least one medical instrument and/or providing further information from within the patient, the intervention system 1 or the intervention device 3 includes an imaging device 4, for example an x-ray device with a C-arm. Both the intervention robot 2 and the imaging device 4 may be operated or controlled at the intervention location 5 where the intervention robot 2 and the imaging device 4 are situated, e.g. by a corresponding local operating device 6. This may be situated e.g. behind a radiation protection shield 7 relative to the imaging device 4, this is configured as an x-ray device.

The medical intervention in the intervention system 1 may be performed in a distributed manner, meaning that in addition to at least one first person 8 at the intervention location, a second person 9 who for example has special clinical expertise may, at a location 10 that is remote from the intervention location 5 and by an operating device 11 there, generate control information for both the intervention robot 2 and the imaging device 4. The remote location 10 may be situated in a different room, a different building, a different town, a different country and/or on a different continent than the intervention location 5.

Between the intervention location 5 and the remote location 10 is a communication connection 12 that may be established via corresponding communication devices 13, e.g. as an internet connection. The communication connection 12 may be used not only to establish visual and/or acoustic communication between the at least one first person and the at least one second person 9, but also to transfer control information that is provided by the second person 9 for the intervention robot 2 and/or the imaging device 4 from the remote location 10 to the intervention location 5, and on the other side to transfer situational data describing the intervention situation from the intervention location 5 to the remote location 10. The situational data may be captured at least partly by a situational data capturing apparatus 14, e.g. a camera that is directed at the patient and the intervention robot 2, but alternatively by the imaging device 4 itself and/or as operating data from the intervention robot 2 and/or other devices employed during the intervention. The situational data provides the second person 9 with an image that is at least to a large extent complete in the case of the intervention robot 2, that operates slowly, though this does not apply in the case of the imaging device 4 since its region of influence and/or effect extends into areas that are not covered by the situational data, particularly with regard to the initiation of the x-radiation and people/objects affected by this and with regard to any movement of recording components, e.g. the C-arm with the attached recording structure including x-ray source and x-ray detector.

The general operation of the intervention system 1 is controlled by a control device 15. In the present example, this is shown at the intervention location 5, but may also be provided at the remote location 10 or at a third, different location. For example, at least the local component of the intervention system 1 at the intervention location 5 may be part of a mobile catheter laboratory.

Owing to the single-channel nature of the communication connection 12, possible latency times on the communication connection 12 in comparison with the response speed of the imaging device 4, and the limited coverage of the situational data, such that only limited monitoring by the second person 9 is possible, further measures are provided to satisfy demands for functional safety in the intervention system 1, enabling the first person 8 to be used for the purpose monitoring the operation of the imaging device 4 on the basis of control information provided by the second person 9 and allowing the presence and monitoring activity of the first person to be technically verified. In order to achieve this, the intervention system 1 includes a signaling device 16 at the intervention location 5 that may be activated by the first person 8, a safeguarding signal is provided as a function of the corresponding activation. The control device 15 allows remote control of the imaging device 4 on the basis of control information provided by the second person 9 by approving the control information only if the safeguarding signal is also present, the safeguarding signal is therefore "AND"-combined with the presence of the control information. This relates at least to functions that relate to the initiation of x-radiation and movement of the recording components (or additionally other components).

The control device 15 is configured to perform the method.

Depending on the specific embodiment variant and implementation, different possibilities for developing the signaling device 16 also exist.

Figure 2:
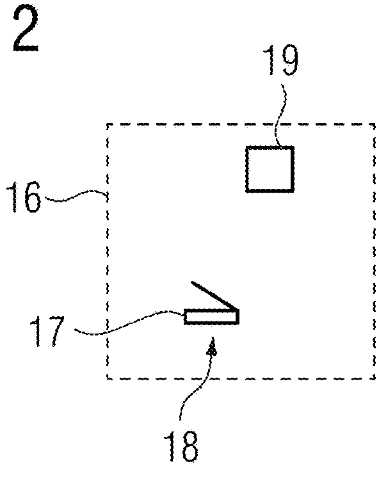
FIG. 2 depicts a signaling device according to an embodiment.

FIG. 2 depicts an embodiment in which the signaling device 16 includes a foot switch 17 as an operating element 18 and an acoustic and/or optical output 19 for outputting indicators. The foot switch 17 may be a local safety switch of the imaging device 4, that must be activated in order that safety-critical functions, i.e. functions related to the initiation of radiation and the movement of components in this case, may be executed. For example, a further corresponding foot switch via which the second person 9 may initiate x-radiation or a movement as specific control information may be provided at the operating device 11.

The operating element 18 simultaneously serves as an emergency-off switch, meaning that if the first person 8 releases the operating element 18, i.e. ceases the activation, the safety-critical functions at the imaging device 4 are disabled immediately and corresponding implementations of control information are terminated. For example, a recording operation involving the emission of x-radiation is ceased.

In order to prevent the first person 8 from avoiding the monitoring obligation, e.g. by mechanically securing the foot switch 17, they must periodically indicate their presence by briefly interrupting the activation of the operating element 18, this requirement is indicated to them by the output 19, i.e. a corresponding indicator output. This may take place optically and/or acoustically. The indicator output and therefore the requirement for an interruption may take place periodically at predefined time intervals, e.g. in the range of 10 to 60 seconds, but does not take place at precisely the same time as control information provided by the second person 9 is implemented, in order to prevent the control information from being accidentally interrupted by the check for presence as a consequence of the further function as an emergency-off switch. The indicator output is followed by a time window during which the brief interruption may be performed by the first person 8, e.g. 1 to 4 seconds. If the brief interruption in the activation of the operating element 18 is not performed, the safeguarding signal is ceased.

Figure 3:
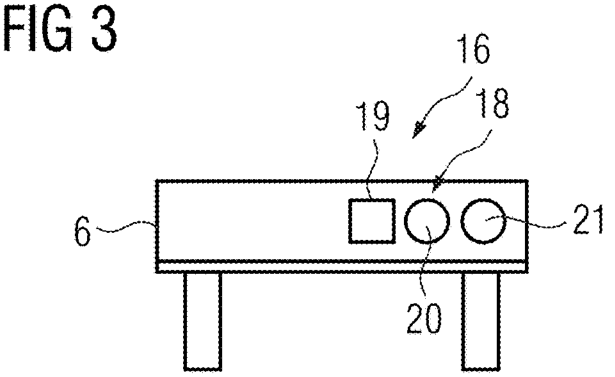
FIG. 3 depicts a signaling device according to an embodiment.

FIG. 3 depicts a second possible development of the signaling device 16 in a second embodiment. By way of example, the operating element 18 here is configured as an operating button 20 and is provided on the operating device 6, this is configured as e.g. an operating console. An optical and/or acoustic output 19 is again assigned to the operating element 18. In this case, the operating element 18 may be used e.g. as a dead man's switch, meaning that in order to indicate the presence and monitoring activity of the first person 8, it must be reactivated in each case at the latest after expiry of a predetermined time period, that again may be e.g. 10 to 60 seconds long. After expiry of this time period, an indicator output may again take place via the output 19. If, however, the operating element 18 acting as a dead man's switch is not reactivated within a time window of e.g. 1 to 4 seconds, the presence of the safeguarding signal is again ceased. It may be seen that the operating element 18 is arranged in the immediate vicinity of an emergency-off switch 21 via which the execution of safety-relevant functions, for example functions relating to the x-radiation and the movement of components here, may be either disabled or stopped if they are already executed. The person 8 is therefore not only situated in a suitable monitoring position but may also react quickly if danger is imminent.

However, the development according to FIG. 3 may also be applied in an embodiment in which individual items of control information, that are provided by the second person 9 and are also perceptible to the first person 8, may be individually confirmed and approved by the operating element 18. One such case is the use of e.g. voice commands that are acoustically received and interpreted by the imaging device 4 itself. In this context, the second person 9 utters a voice command that is output via a corresponding loudspeaker at the intervention location 5, e.g. the output 19, and may be heard by both the imaging device 4 and the first person 8. By activating the operating element 18, the first person 8 may generate the safeguarding signal that is specific to the voice command, such that the corresponding control information may be implemented.

Figure 4:
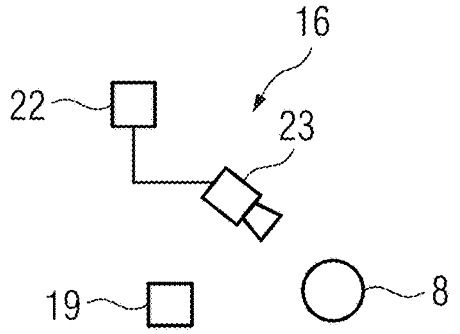
FIG. 4 depicts a signaling device according to an embodiment.

FIG. 4 depicts a third possible development of the signaling device 19, in which the operating element 18 is not realized in the form of hardware but in the form of gesture recognition by a gesture recognition unit 22 that evaluates image data that relates to the first person 8 and is provided by a 3D camera 23. In the first embodiment cited above, if the operating element 18 must be lastingly activated, and is virtual in this case, use may be made of e.g. specific gestures that are continuously maintained, e.g. a raised hand, whereby a lowering of the hand then constitutes a cessation of the activation. However, gestures for one-time activation of the operating element, that is virtual here, are also conceivable for the second and third embodiment variants, e.g. an "OK" sign made with the fingers and/or a "thumbs up" sign. Accordingly, an output 19 may also be provided here if an implementation such as a dead man's switch or similar to an automatic vigilance device is used.

Figure 5:
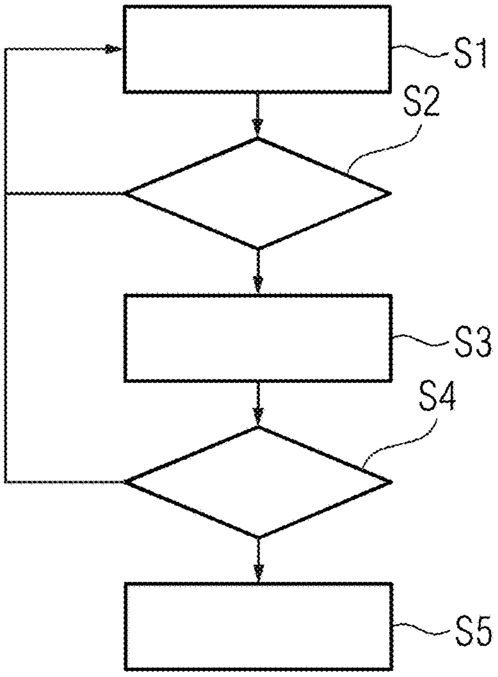
FIG. 5 depicts a sequence plan of an embodiment of a method.
Figure 6:
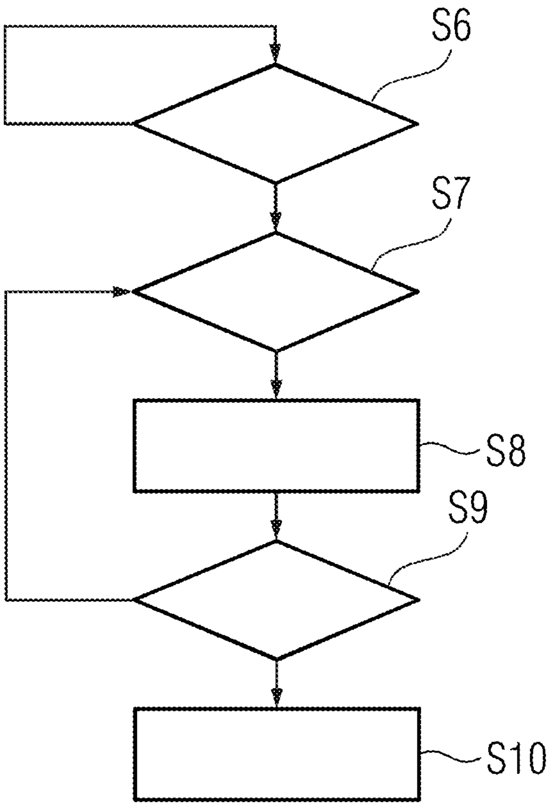
FIG. 6 depicts a sequence plan of an embodiment of the method.
Figure 7:
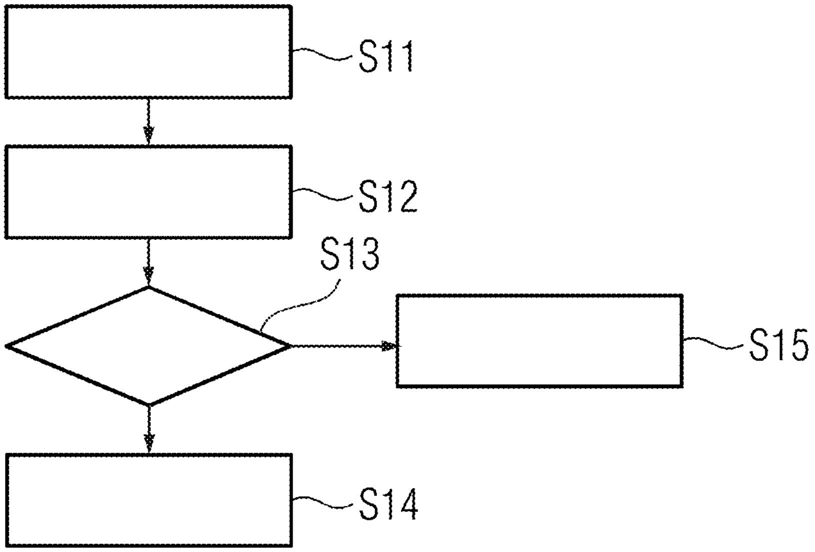
FIG. 7 depicts a sequence plan of an embodiment of the method.

The various embodiments indicated above are now explained further by the sequence plans in FIGS. 5 to 7.

FIG. 5 depicts a sequence plan describing a first embodiment of the method using the intervention system 1. In this case, continuous activation of the operating element 18 of the signaling device 16 takes place in a step S1, such that the safeguarding signal is generated. In a step S2, it is checked whether a predetermined time interval has elapsed since the start of the activation of the operating element 18. If this is the case, an optical and/or acoustic indicator output to the first person 8 takes place in a step S3, indicating that a brief interruption in the activation of the operating element 18 must take place, the interruption is suppressed only if control information is implemented at precisely the same time. In this case, the indicator output takes place after cessation of the corresponding implementation. In a step S4, it is checked whether a brief interruption in the activation of the operating element 18 took place as an output within a predetermined time window. If this is the case, the sequence returns to step S1 again; if it is not the case, the presence of the safeguarding signal is ceased.

In the second embodiment as per FIG. 6, the operating element 18 is used as a dead man's switch. It is therefore checked in a step S6 whether activation of the operating element 18 has occurred. If this is the case, a predetermined time period is allowed to elapse in a step S7, during which the safeguarding signal is present. Following expiry of the predetermined time period, an indicator output takes place via the output 19 in the step S8, thereby indicating to the first person 8 in a similar manner to step S3 that the operating element 18 must be activated again. In a step S9, it is monitored whether the reactivation of the operating element 18 takes place within a predetermined time window. If this is the case, the sequence returns to step S7, otherwise the presence of the safeguarding signal is ceased in the step S10.

FIG. 7 depicts a sequence plan for a third embodiment of the method. In a step S11 here, the second person 9 gives a voice command, e.g. via a microphone of the operating device 11. In a step S12, this voice command is output to both the imaging device 4 and the first person 8 in an acoustically perceptible manner at the intervention location 5. In a step S13, it is then checked whether the monitoring first person 8 activates the operating element 18 in order to confirm the voice command within a predetermined time interval, e.g. 2 to 5 seconds. If this activation does not take place, the control information (i.e. the voice command) is not implemented. If this activation does though take place, the safeguarding signal is generated in the step S15 and the imaging device 4 may, by the control device 15 if applicable, interpret the voice command and implement the corresponding control information.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method comprising:

generating control information for remote control of an intervention device that is to be used during an intervention at an intervention location, wherein at least one first person is present at the intervention location and at least one second person is present at a remote location that is remote from the intervention location for cooperation during the intervention;

transmitting the control information provided by the second person from the remote location to the intervention location by a communication connection; and controlling the intervention device with the control information only when a safeguarding signal is activated that indicates a monitoring activity of the first person and is output by a signaling device is activated by the first person, wherein the signaling device comprises an operating element that must be lastingly activated by the first person to activate the signaling device, wherein when the operating element is deactivated longer than a predetermined time duration, a drivability of the intervention device is suspended or the intervention device is at least partly deactivated.

2. The method of claim 1, further comprising:

recording situational data by at least one situational data capturing apparatus; and transmitting the situational data to the remote location where it is displayed to the second person, wherein the situational data does not cover an entire region of influence and/or region of effect of the intervention device, and/or that the intervention device is an imaging device comprising a radiation-based and/or mobile recording component that is provided in addition to an intervention robot that is remotely controllable.

3. The method of claim 1, wherein the operating element comprises a foot switch.

4. The method of claim 1, further comprising:

prompting the first person by an indicator output interruption, wherein the safeguarding signal is deactivated if the indicator output interruption is not detected within a time window which follows the indicator output interruption.

5. The method of claim 1 wherein when checking a presence of the first person by an indicator output prompting an interruption in an activation of the operating element, no indicator output takes place while control information provided by the second person is being implemented.

6. The method of claim 1, wherein the signaling device comprises an operating element configured as a dead man's switch, wherein the safeguarding signal is generated when activation of the operating element is detected.

7. The method of claim 6, wherein the operating element is situated in a vicinity of an emergency-off switch of the intervention device.

8. The method of claim 6, wherein the safeguarding signal is generated for a predetermined time period following activation of the operating element, wherein an indicator output takes place after the predetermined time period expires unless a further activation of the operating element is detected, wherein the safeguarding signal is ceased when a time window following the indicator output has elapsed.

9. The method of claim 1, wherein the control information is sent as a voice command that is evaluated by the intervention device, wherein the voice command is output in a manner that is also audible to the first person at the intervention location, and the safeguarding signal is generated in a manner that is specific to the voice command when an operating element of the signaling device is activated.

10. The method of claim 1, wherein image data of the first person is evaluated by the signaling device in order to detect gestures of the first person that identify a signal generation.

11. A system comprising:

an intervention device at an intervention location, the intervention device used for an intervention, wherein the intervention device is operated by a first person at the intervention location;

an operating device at a remote location that is remote from the intervention location, wherein the operating device is used by a second person to provide control information for the intervention device;

a communication connection configured to send the control information from the remote location to the intervention location;

a control device that is configured to use the control information to control the intervention device; and a signaling device comprising an operating element that must be lastingly activated, that when activated by the first person generates a safeguarding signal, wherein the control device is configured to use the control information for controlling the intervention device only if the safeguarding signal that indicates a monitoring activity of the first person is present, wherein the signaling device is further configured to prompt the first person by an indicator output interruption, wherein the safeguarding signal is deactivated if the indicator output interruption is not detected within a time window which follows the indicator output interruption.

12. The system of claim 11, further comprising a situational data capturing apparatus that is configured to record and transmit situation data to the remote location where it is displayed to the second person, wherein the situational data does not cover an entire region of influence and/or region of effect of the intervention device, and/or that the intervention device is an imaging device comprising a radiation-based and/or mobile recording component that is provided in addition to an intervention robot that is remotely controllable.

13. The system of claim 11, wherein the operating element comprises a foot switch.

14. The system of claim 11, wherein when the operating element is deactivated longer than a predetermined time duration, a drivability of the intervention device is suspended or the intervention device is at least partly deactivated.

15. The system of claim 14, wherein when checking a presence of the first person by an indicator output prompting an interruption in an activation of the operating element, no indicator output takes place while control information provided by the second person is being implemented.

16. The system of claim 11, wherein the signaling device comprises an operating element configured as a dead man's switch, wherein the safeguarding signal is generated when activation of the operating element is detected.

17. A computer-implemented method comprising:

generating control information for remote control of an intervention device that is to be used during an intervention at an intervention location, wherein at least one first person is present at the intervention location and at least one second person is present at a remote location that is remote from the intervention location for cooperation during the intervention;

transmitting the control information provided by the second person from the remote location to the intervention location by a communication connection; and evaluating, by a signaling device, image data of the first person to detect gestures of the first person that indicate a safeguarding signal generation;

controlling the intervention device with the control information only when the safeguarding signal is activated that indicates a monitoring activity of the first person.

* * * * *